(12) United States Patent
Argo et al.

(10) Patent No.: US 7,998,495 B2
(45) Date of Patent: Aug. 16, 2011

(54) ANTIMICROBIAL TISSUE PRODUCTS WITH REDUCED SKIN IRRITATION POTENTIAL

(75) Inventors: Brian Patrick Argo, Uniontown, OH (US); Timothy Maurice McFarland, Neenah, WI (US); Pamela Mary Thompson, Greenville, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 528 days.

(21) Appl. No.: 12/006,653

(22) Filed: Jan. 3, 2008

(65) Prior Publication Data

US 2008/0107716 A1   May 8, 2008

Related U.S. Application Data

(62) Division of application No. 10/861,551, filed on Jun. 4, 2004, now abandoned.

(51) Int. Cl.
*A61K 9/70*   (2006.01)
*A61K 8/00*   (2006.01)

(52) U.S. Cl. ........ 424/402; 424/401; 424/404; 510/130; 510/137; 510/143; 510/155; 510/157

(58) Field of Classification Search .................. 424/402, 424/401, 404; 510/130, 137, 143, 155, 157
See application file for complete search history.

(56) References Cited

U.S. PATENT DOCUMENTS

| 3,953,638 | A  | 4/1976  | Kemp |
| 4,100,324 | A  | 7/1978  | Anderson et al. |
| 4,426,417 | A  | 1/1984  | Meitner et al. |
| 4,637,859 | A  | 1/1987  | Trokhan |
| 4,738,847 | A  | 4/1988  | Rothe et al. |
| 4,764,418 | A  | 8/1988  | Kuenn et al. |
| 4,824,689 | A  | 4/1989  | Kuenn et al. |
| 4,828,912 | A  | 5/1989  | Hossain et al. |
| 4,865,855 | A  | 9/1989  | Hansen et al. |
| 4,897,304 | A  | 1/1990  | Hossain et al. |
| 4,975,217 | A  | 12/1990 | Brown-Skrobot et al. |
| 5,048,589 | A  | 9/1991  | Cook et al. |
| 5,324,575 | A  | 6/1994  | Sultze et al. |
| 5,336,373 | A  | 8/1994  | Scattolino et al. |
| 5,556,509 | A  | 9/1996  | Trokhan et al. |
| 5,650,218 | A  | 7/1997  | Krzysik et al. |
| 5,656,134 | A  | 8/1997  | Marinack et al. |
| 5,665,426 | A  | 9/1997  | Krzysik et al. |
| 5,685,954 | A  | 11/1997 | Marinack et al. |
| 5,690,788 | A  | 11/1997 | Marinack et al. |
| 5,709,775 | A  | 1/1998  | Trokhan et al. |
| 5,776,312 | A  | 7/1998  | Trokhan et al. |
| 5,779,860 | A  | 7/1998  | Hollenberg et al. |
| 5,814,190 | A  | 9/1998  | Van Phan |
| 5,837,103 | A  | 11/1998 | Trokhan et al. |
| 5,846,379 | A  | 12/1998 | Ampulski et al. |
| 5,869,075 | A  | 2/1999  | Krzysik |
| 5,871,887 | A  | 2/1999  | Trokhan et al. |
| 5,885,415 | A  | 3/1999  | Marinack et al. |
| 5,885,417 | A  | 3/1999  | Marinack et al. |
| 6,080,279 | A  | 6/2000  | Hada et al. |
| 6,083,346 | A  | 7/2000  | Hermans et al. |
| 6,096,169 | A  | 8/2000  | Hermans et al. |
| 6,118,041 | A  | 9/2000  | Roe et al. |
| 6,146,648 | A  | 11/2000 | Bret et al. |
| 6,149,934 | A  | 11/2000 | Krzysik et al. |
| 6,153,208 | A  | 11/2000 | McAtee et al. |
| 6,156,024 | A  | 12/2000 | Schulte et al. |
| 6,179,961 | B1 | 1/2001  | Ficke et al. |
| 6,183,766 | B1 | 2/2001  | Sine et al. |
| 6,207,014 | B1 | 3/2001  | De Haut et al. |
| 6,238,682 | B1 | 5/2001  | Klofta et al. |
| 6,261,580 | B1 | 7/2001  | Lehrter et al. |
| 6,287,581 | B1 | 9/2001  | Krzysik et al. |
| 6,296,862 | B1 | 10/2001 | Paul et al. |
| 6,316,013 | B1 | 11/2001 | Paul et al. |
| 6,537,663 | B1 | 3/2003  | Chang et al. |
| 6,683,143 | B1 | 1/2004  | Mumick et al. |
| 7,132,379 | B2 | 11/2006 | Shanklin |
| 2001/0037100 | A1 | 11/2001 | Shanklin |
| 2002/0006434 | A1 | 1/2002  | Shanklin et al. |
| 2002/0127937 | A1 | 9/2002  | Lange et al. |
| 2005/0005883 | A1 | 1/2005  | Jiang |

FOREIGN PATENT DOCUMENTS

| CA | 1 188 225   |     | 6/1985  |
| EP | 0 631 014   | B1  | 10/1997 |
| EP | 1 029 977   | A1  | 8/2000  |
| EP | 0 677 612   | B1  | 9/2000  |

(Continued)

OTHER PUBLICATIONS

Yoneto, K. et al. "Mechanistic studies of 1-alkyl-2-pyrrolidones as skin permeation enhancing agents", J. Pharm. Sci. 1995, Mar;(84):3-312-7, abstract.*

"Sodium Lauryl Sulfate," *The Merck Index—An Encyclopedia of Chemicals, Drugs, and Biologicals*, 13th Edition, Merck & Co., Inc., 2001, p. 1543.

*Primary Examiner* — Gina C Yu

(74) *Attorney, Agent, or Firm* — R. Joseph Foster, III

(57) ABSTRACT

A non-irritating antimicrobial multi-layer or multi-ply tissue product made by treating an inner layer or ply or an inner surface of an inner layer or ply with one or more antimicrobial agents and treating the one or more outer layers or plies or the outer surfaces of the layers or plies with one or more irritation-inhibiting agents, and methods of making and using the same. The antimicrobial agent will remain confined to the inner portion of the tissue product, thereby preventing irritation to the user, and the irritation-inhibiting composition treated layer(s) or ply(s) provides a pleasing, soothing, non-irritating tactile quality to the tissue product. The non-irritating antimicrobial multi-layer or multi-ply tissue product further comprises an absorption enhancing agent. In one embodiment, the irritation-inhibiting composition comprises an oil, in which case the tissue product will also entrap any absorbed contaminant, holding it in contact with the antimicrobial agent.

9 Claims, 6 Drawing Sheets

FOREIGN PATENT DOCUMENTS

| | | |
|---|---|---|
| EP | 1 050 297 A2 | 11/2000 |
| EP | 1 153 619 A1 | 11/2001 |
| GB | 1117216 | 6/1968 |
| WO | WO 99/45771 A1 | 9/1999 |
| WO | WO 00/49228 A1 | 8/2000 |
| WO | WO 00/57843 A2 | 10/2000 |
| WO | WO 00/64407 A1 | 11/2000 |
| WO | WO 00/64500 A1 | 11/2000 |
| WO | WO 00/64503 A1 | 11/2000 |
| WO | WO 00/69482 A1 | 11/2000 |
| WO | WO 00/69485 A1 | 11/2000 |
| WO | WO 01/28337 A2 | 4/2001 |
| WO | WO 01/29315 A1 | 4/2001 |
| WO | WO 01/47699 A1 | 7/2001 |
| WO | WO 01/49117 A2 | 7/2001 |
| WO | WO 01/83876 A1 | 11/2001 |
| WO | WO 02/34305 A2 | 5/2002 |

* cited by examiner

ANTIMICROBIAL TISSUE PRODUCTS WITH REDUCED SKIN IRRITATION POTENTIAL

This application is a divisional of application Ser. No. 10/861,551 filed on Jun. 4, 2004.

BACKGROUND

Many of the known antimicrobial agents are irritating to users' skin. Nonwoven products, such as tissue products, treated with antimicrobial agents may be irritating to the users' skin because the antimicrobial agents come in contact with the skin when the products are used.

Some products where the antimicrobial agents are applied to an inner ply still cause irritation to the users' skin because the compositions containing the antimicrobial agents degrade the tactile properties of the products, leaving the products harsh.

Irritation caused by the inclusion of antimicrobial agents in consumer tissue products is a persistent problem. There have been attempts to ameliorate this problem by mixing the antimicrobial agents with lotions or emollients. Products comprising the mixture of antimicrobial agents and lotions or emollients may also have a high potential for irritation because the antimicrobial agents are on the surface of the product and are intentionally transferred with the lotions or emollients to the user, resulting in prolonged contact with the antimicrobial agents, the source of irritation.

SUMMARY

The present invention provides tissue products that are soft, non-irritating, and capable of killing or otherwise inactivating the contaminants. More specifically, the present invention provides a multi-layer or multi-ply tissue product having an outer surface, layer, or ply treated with an irritation-inhibiting composition comprising at least an irritation-inhibiting agent and an inner surface, layer, or ply treated with an antimicrobial agent. The present invention generally relates to tissue products such as facial tissue, paper towels, bath tissue, napkins, or wipes which comprise multiple layers or plies of material.

In one aspect of the present invention, the tissue product includes a plurality of layers having at least one of the layers defining an outer layer and at least one of the layers defining an inner layer. An irritation-inhibiting composition comprising at least one or more irritation-inhibiting agents is applied to at least one outer layer and an antimicrobial effective amount of one or more antimicrobial agents applied to at least one inner layer.

In a further aspect of the present invention, a method is provided for making the non-irritating, antimicrobial, multi-layer tissue product. In yet another aspect of the present invention, a method is provided for using the non-irritating, antimicrobial, multi-layer tissue product to inhibit the spread of illness.

In another aspect of the present invention, the tissue product includes a plurality of plies having at least one of the plies defining an outer ply and at least one of the plies having a surface defining an inner surface. An irritation-inhibiting composition comprising at least one or more irritation-inhibiting agents is applied to at least one outer ply and an antimicrobial effective amount of one or more antimicrobial agents applied to at least one inner surface.

In a further aspect of the present invention, a method is provided for making the non-irritating, antimicrobial, multi-ply tissue product. In yet another aspect of the present invention, a method is provided for using the non-irritating, antimicrobial, multi-ply tissue to inhibit the spread of illness.

Other aspects of the present invention will be apparent in view of the following description of the embodiments and the accompanying drawings.

DETAILED DESCRIPTION OF THE EMBODIMENTS OF THE PRESENT INVENTION

Figure 1:
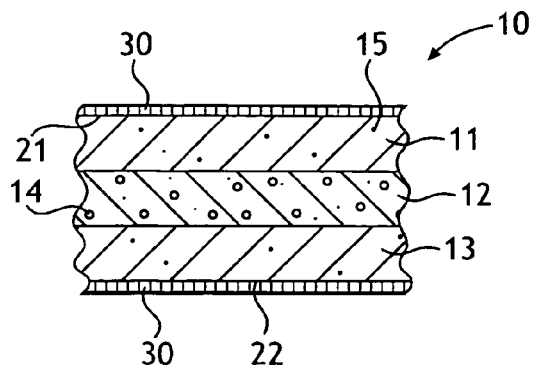
FIG. 1 is a diagram of a tissue product having three layers, including two outer layers, according to one embodiment of the present invention.

Referring now to the accompanying drawings and initially to FIG. 1, a multi-layer tissue product is shown generally at 10. The term "layer" refers to a plurality of strata of different fibers, chemical treatments, etc., within a ply.

In the embodiment shown in FIG. 1, the multi-layer tissue product 10 has a first outer layer 11, an inner layer 12, and a second outer layer 13. The first outer layer 11 and the second outer layer 13 each have an outwardly facing surface defining outer surfaces 21 and 22, respectively, of the tissue product 10. The inner layer 12 has outwardly facing surfaces defining inner surfaces 23 and 24.

The layers of the tissue product 10 may be made from natural fibers, synthetic fibers, or mixtures thereof. For example, some suitable natural fibers may include, but are not limited to, nonwoody fibers, such as abaca, sabai grass, milkweed floss fibers, pineapple leaf fibers; softwood fibers, such as northern and southern softwood kraft fibers; and, hardwood fibers, such as eucalyptus, maple, birch, aspen, and the like. Illustrative examples of other suitable pulps include southern pines, red cedar, hemlock, and black spruce. Commercially available long pulp fibers that may be used in the present invention include those available from Kimberly-Clark Corporation under the trade designations "Longlac-19". In addition, furnishes including recycled fibers may also be utilized. Moreover, some suitable synthetic fibers may include, but are not limited to, hydrophilic synthetic fibers, such as rayon fibers and ethylene vinyl alcohol copolymer fibers, as well as hydrophobic synthetic fibers, such as polyolefin fibers. The multi-layer tissue product 10 may include a multi-layer facial tissue, bath tissue, paper towel, napkin, wipe, and the like.

The inner layer 12 may be treated with an antimicrobial effective amount of an antimicrobial agent 14. The term "antimicrobial effective amount" as used herein means an amount of an antimicrobial agent 14 effective to reduce the rate at which targeted viruses or microbes reproduce or to reduce the population of the viruses or microbes.

The antimicrobial agent 14 serves to kill or otherwise inactivate any contaminant, such as viruses, bacteria, fungi or other microorganism, that are contacted with or absorbed into the tissue product 10 during use, thereby inhibiting the spread of disease, such as a viral infection. In one embodiment of the present invention, a user contacts the multi-layer product 10 with a contaminant 15, thereby contacting the contaminant 15 with the antimicrobial agent 14. The antimicrobial agent 14 is typically confined to the inner layer 12 of the multi-layer tissue product 10, thus preventing its transfer to the skin and resultant irritation.

The term "contaminant" as used herein means refers to soils, microbes, gram positive and gram negative bacteria, yeast, viruses, feces, urine, menses, enzymes, toxins, endotoxins, blood, protozoan, organic and inorganic materials, and other organic and inorganic soils. In another embodiment of the present invention, the multi-layer tissue product 10 inhibits the spread of illness. The multi-layer tissue product 10 may be a facial tissue. A user contacts the multi-layer tissue product 10 with a contaminant 15 in the form of a bodily discharge, such as a nasal discharge, wherein the contaminant 15 is brought into contact with the antimicrobial agent 14.

At least one of the outer surfaces 21 and 22 of the first and second outer layers 11 and 13, respectively, is treated with an irritation-inhibiting composition 30, which may give the first and second outer layers 11 and 13 a softer feel. In one embodiment, the irritation-inhibiting composition 30 comprises at least an irritation-inhibiting agent selected from emollients, glycerin and its derivatives, glycols and their derivatives, liquid polyethylene glycols, ethoxylated polydimethylsiloxanes, quaternary ammonium compounds, botanical extracts with anti-irritant properties, waxes, solid fatty acid esters, solid fatty alcohols, hydrogenated animal or vegetable oils and their derivatives, lotion compositions, or mixtures thereof. The irritation-inhibiting composition 30 further comprises an absorption enhancing agent. The irritation-inhibiting composition 30 may reside on at least one of the outer surfaces 21 or 22 of the substrate to which they are applied, either as a result of hydrogen bonding, charge attraction, or other chemical or physical interactions, thereby providing a softness benefit on the surfaces 21 or 22. The contaminant 15 is readily absorbed into the inner layer 12 wherein the contaminant 15 comes into contact with the antimicrobial agent 14, inactivating the contaminant 15 and preventing further exposure to the user.

The irritation-inhibiting composition 30 may readily transfer from the multi-layer tissue product 10 to the user's skin. Such a transfer of the irritation-inhibiting composition 30 may provide skin enhancing benefits to the user's skin. In the event that the antimicrobial agent 14 is transferred from the multi-layer tissue product 10 to the user's skin, the irritation-inhibiting composition 30 may serve as a barrier, provide soothing qualities, or otherwise provide protection for the user's skin.

Figure 1C:
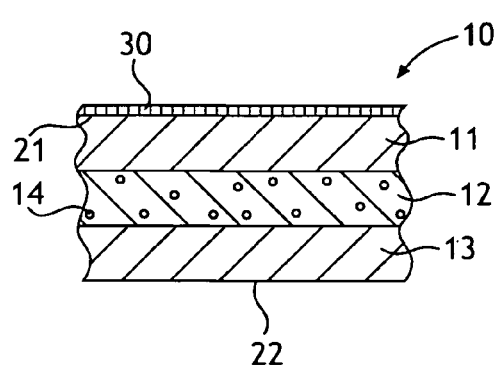
FIGS. 1A-1I are diagrams showing different configurations of a tissue product having three layers, including two outer layers, according to one embodiment of the present invention.
Figure 1A:
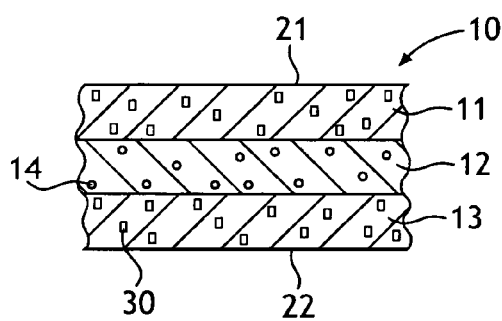

FIG. 1A shows a multi-layer tissue product 10 having a first outer layer 11, an inner layer 12, and a second outer layer 13. The inner layer 12 is treated with an antimicrobial effective amount of an antimicrobial agent 14. The first and second outer layers 11 and 13, respectively, are treated with an irritation-inhibiting composition 30.

Figure 1D:
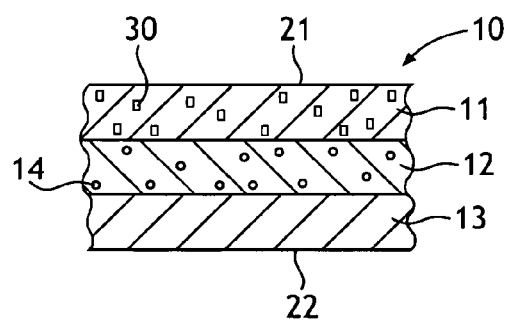
Figure 1B:
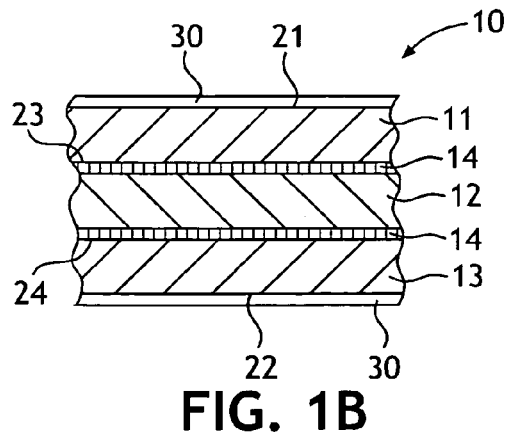

FIG. 1B shows a multi-layer tissue product 10 having a first outer layer 11, an inner layer 12, and a second outer layer 13. The inner surfaces 23 and 24 of the inner layer 12 are treated with an antimicrobial effective amount of an antimicrobial agent 14. The outer surfaces 21 and 22 of the first and second outer layers 11 and 13, respectively, are treated with an irritation-inhibiting composition 30.

FIG. 1C shows a multi-layer tissue product 10 having a first outer layer 11, an inner layer 12, and a second outer layer 13. The inner layer 12 is treated with an antimicrobial effective amount of an antimicrobial agent 14. The outer surface 21 of the first outer layer 11 is treated with an irritation-inhibiting composition 30. It is understood that the outer surface 22 of the second outer layer 13 may be treated with the irritation-inhibiting composition 30 in place of the treatment of the outer surface 21 of the first outer layer 11.

FIG. 1D shows a multi-layer tissue product 10 having a first outer layer 11, an inner layer 12, and a second outer layer 13. The inner layer 12 is treated with an antimicrobial effective amount of an antimicrobial agent 14. The first outer layer 11 is treated with an irritation-inhibiting composition 30. It is understood that the second outer layer 13 may be treated with the irritation-inhibiting composition 30 in place of the treatment of the first outer layer 11.

Figure 1E:
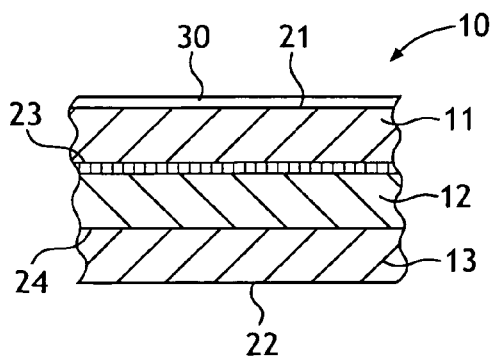

FIG. 1E shows a multi-layer tissue product 10 having a first outer layer 11, an inner layer 12, and a second outer layer 13. The inner surface 23 of the inner layer 12 is treated with an antimicrobial effective amount of an antimicrobial agent 14. The outer surface 21 of the first outer layer 11 is treated with an irritation-inhibiting composition 30. It is understood that the outer surface 22 of the second outer layer 13 may be treated with the irritation-inhibiting composition 30 in place of the treatment of the outer surface 21 of the first outer layer 11. Additionally, it is understood that the inner surface 24 of the inner layer 12 may be treated with the antimicrobial effective amount of the antimicrobial agent 14 in place of the treatment of the inner surface 23 of the inner layer 12.

Figure 1F:
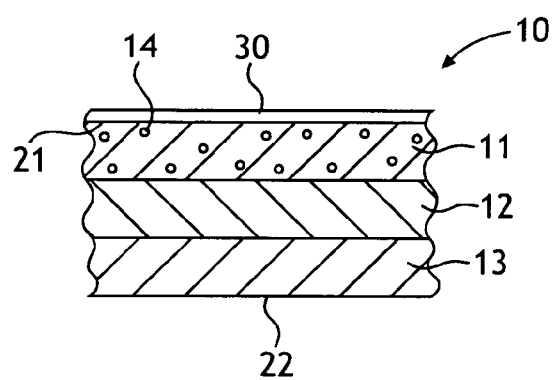

FIG. 1F shows a multi-layer tissue product 10 having a first outer layer 11, an inner layer 12, and a second outer layer 13. The first outer layer 11 is treated with an antimicrobial effective amount of an antimicrobial agent 14. The outer surface 21 of the first outer layer 11 is treated with an irritation-inhibiting composition 30. It is understood that the outer surface 22 of the second outer layer 13 may be treated with the irritation-inhibiting composition 30 in place of the treatment of the outer surface 21 of the first outer layer 11. Additionally, it is understood that the second outer layer 13 may be treated with the antimicrobial effective amount of the antimicrobial agent 14 in place of the treatment of the first outer layer 11.

Figure 1H:
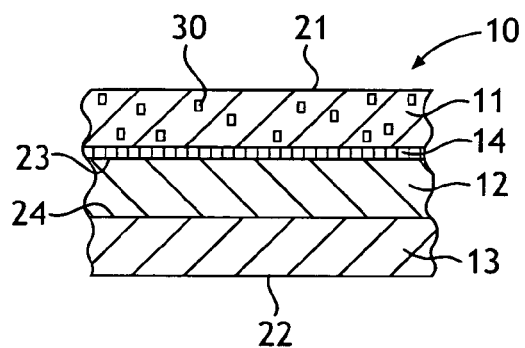
Figure 1G:
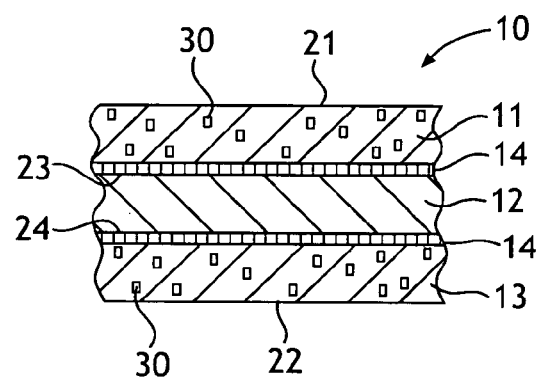

FIG. 1G shows a multi-layer tissue product 10 having a first outer layer 11, an inner layer 12, and a second outer layer 13. The inner surfaces 23 and 24 of the inner layer 12 are treated with an antimicrobial effective amount of an antimicrobial agent 14. The first and second outer layers 11 and 13 are treated with an irritation-inhibiting composition 30.

FIG. 1H shows a multi-layer tissue product 10 having a first outer layer 11, an inner layer 12, and a second outer layer 13. The inner surface 23 of the inner layer 12 is treated with an antimicrobial effective amount of an antimicrobial agent 14. The first outer layer 11 is treated with an irritation-inhibiting composition 30. It is understood that the second outer layer 13 may be treated with the irritation-inhibiting composition 30 in place of the treatment of the first outer layer 11. Additionally, it is understood that the inner surface 24 of the inner layer 12 may be treated with the antimicrobial effective amount of the antimicrobial agent 14 in place of the treatment of the inner surface 23 of the inner layer 12.

Figure 1I:
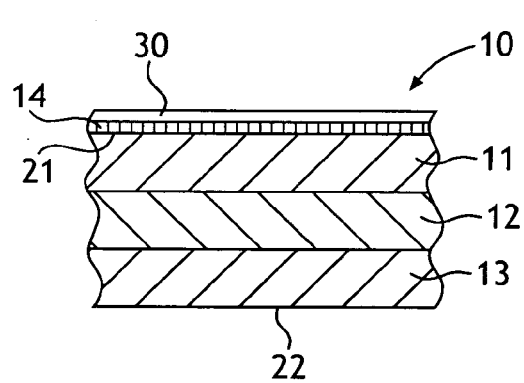

FIG. 1I shows a multi-layer tissue product 10 having a first outer layer 11, an inner layer 12, and a second outer layer 13. The outer surface 21 of the first outer layer 11 is treated with an antimicrobial effective amount of an antimicrobial agent 14. The outer surface 21 of the first outer layer 11 is then treated with an irritation-inhibiting composition 30 such that the irritation-inhibiting agent 30 is applied over the antimicrobial agent 14. It is understood that the outer surface 22 of the second outer layer 13 may be treated in the antimicrobial effective amount of the antimicrobial agent 14 in place of the treatment of the outer surface 21 of the first outer layer 11.

The particulars of both the antimicrobial agent 14 and the irritation-inhibiting composition 30 will be discussed in detail below.

Figure 2B:
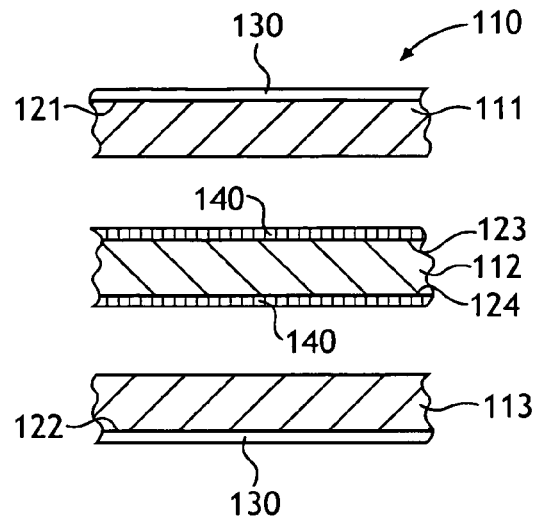
FIGS. 2A-2G are diagrams showing different configurations of a tissue product having three plies, including two outer plies, according to another embodiment of the present invention.
Figure 2:
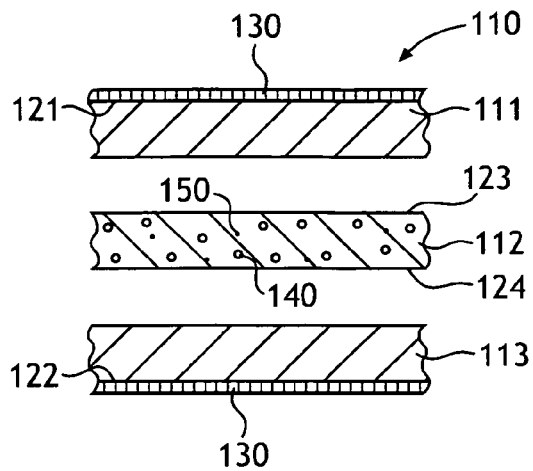
FIG. 2 is a diagram of a tissue product having three plies, including two outer plies, according to another embodiment of the present invention.

Referring now to the accompanying drawings and initially to FIG. 2, a multi-ply tissue product is shown generally at 110. The term "plies" refers to discrete product elements arranged in juxtaposition to each other. The term may refer to a plurality of web-like components such as in a multi-ply facial tissue, bath tissue, paper towel, wipe, or napkin.

In the embodiment shown in FIG. 2, the multi-ply tissue product 110 has a first outer ply 111, an inner ply 112, and a second outer ply 113. The first outer ply 111 and the second outer ply 113 each have an outwardly facing surface defining outer surfaces 121 and 122, respectively. The inner ply 112 has two outwardly facing surfaces defining the inner surfaces 123 and 124.

The outer and inner plies 111, 112, and 113 of the multi-ply tissue product 110 may be may be made from the fibers as disclosed above. The multi-ply tissue product 110 may include a multi-layer facial tissue, bath tissue, paper towel, napkin, wipes, and the like. The outer and inner plies 111, 112, and 113 may be made of the same fibers or mixtures of fibers or made from different fibers or mixtures of fibers than is used in one or more of the other plies.

The inner surfaces 123 and 124 of the inner ply 112 may be treated with an antimicrobial effective amount of an antimicrobial agent 140. In a one embodiment of the present invention, a user contacts the multi-ply tissue product 110 with a contaminant 150, thereby bringing the contaminant 150 into contact with the antimicrobial agent 140. The antimicrobial agent 140 is typically confined to the inner ply(s) 112 of the multi-ply tissue product 110, thus preventing the transfer of the antimicrobial agent 140 to the skin and resultant irritation.

In another embodiment of the present invention, the multi-ply tissue product 110 inhibits the spread of illness. The multi-ply tissue product 110 may be a facial tissue. A user contacts the multi-ply tissue product 110 with a contaminant 150 in the form of a bodily discharge, such as a nasal discharge, and brings the contaminant 150 into contact with the antimicrobial agent 140.

At least one of the outer surfaces 121 and 122 of the first and second outer plies 111 and 113, respectively, is treated with an irritation-inhibiting composition 130, which gives the first and second outer plies 111 and 113 of the tissue product 110 a softer feel. In a one embodiment, the irritation-inhibiting composition 130 comprising at least an irritation-inhibiting agent selected from an emollient, wax, solid fatty acid ester, fatty alcohol, hydrogenated animal or vegetable oil, lotion formulation, or mixture thereof. The irritation-inhibiting composition 130 may reside on at least one of the outer surfaces 121 and 122 of the substrate to which they are applied, either as a result of hydrogen bonding, charge attraction, or other chemical interaction, thereby providing a softness benefit on the outer surfaces 121 and 122. The contaminant 150 is readily absorbed onto at least one of the inner surfaces 123 and 124 of the inner ply 112 or by the inner ply 112 wherein the contaminant 150 comes into contact with the antimicrobial agent 140, thus killing or otherwise inactivating the microorganisms within the contaminant 150 and preventing further exposure to the user.

Figure 2A:
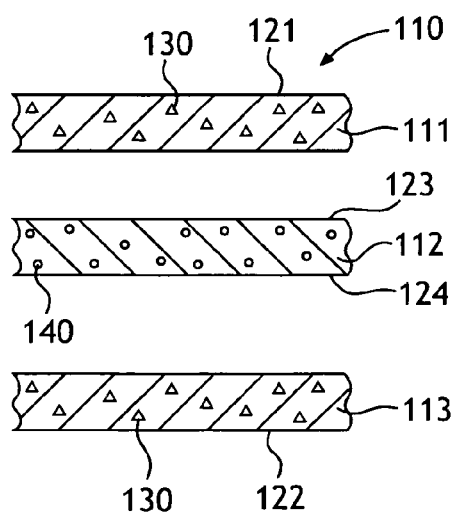

FIG. 2A shows a multi-ply tissue product 110 having a first outer ply 111, an inner ply 112, and a second outer ply 113. The inner ply 112 is treated with an antimicrobial effective amount of an antimicrobial agent 140. The first and second outer plies 111 and 113 are treated with an irritation-inhibiting composition 130.

FIG. 2B shows a multi-ply tissue product 110 having a first outer ply 111, an inner ply 112, and a second outer ply 113. The inner surfaces 123 and 124 of the inner ply 112 are treated with an antimicrobial effective amount of an antimicrobial agent 140. The outer surfaces 121 and 122 of the first and second outer plies 111 and 113, respectively, are treated with an irritation-inhibiting composition 130.

Figure 2C:
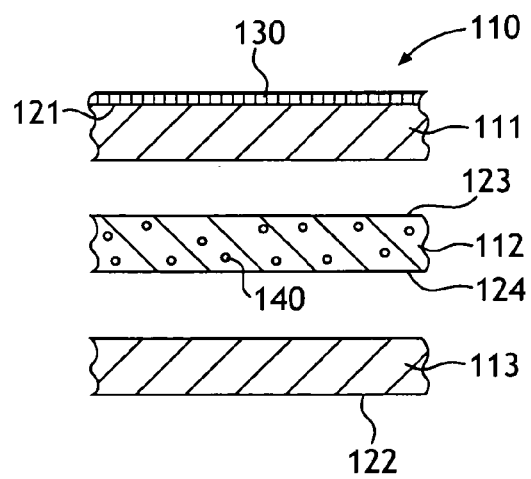

FIG. 2C shows a multi-ply tissue product 110 having a first outer ply 111, an inner ply 112, and a second outer ply 113. The inner ply 112 is treated with an antimicrobial effective amount of an antimicrobial agent 140. The outer surface 121 of the first outer ply 111 is treated with an irritation-inhibiting composition 130. It is understood that the outer surface 122 of the second outer ply 113 may be treated with the irritation-inhibiting composition 130 in place of the treatment of the outer surface 121 of the first outer ply 111.

Figure 2D:
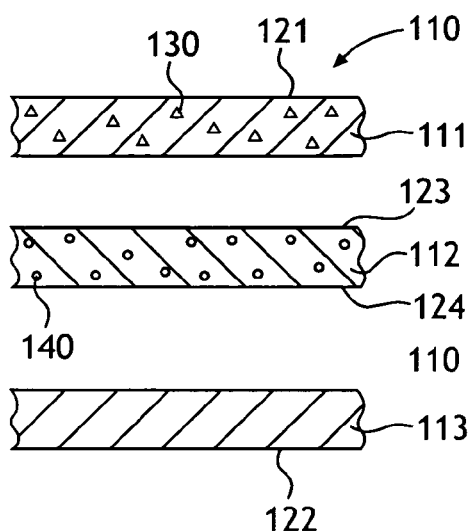

FIG. 2D shows a multi-ply tissue product 110 having a first outer ply 111, an inner ply 112, and a second outer ply 113. The inner ply 112 is treated with an antimicrobial effective amount of an antimicrobial agent 140. The first outer ply 111 is treated with an irritation-inhibiting composition 130. It is understood that the second outer ply 113 may be treated with the irritation-inhibiting composition 130 in place of the treatment of the first outer ply 111.

Figure 2F:
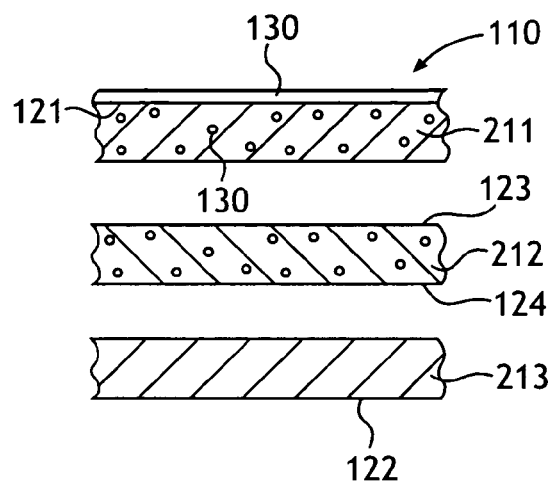
Figure 2E:
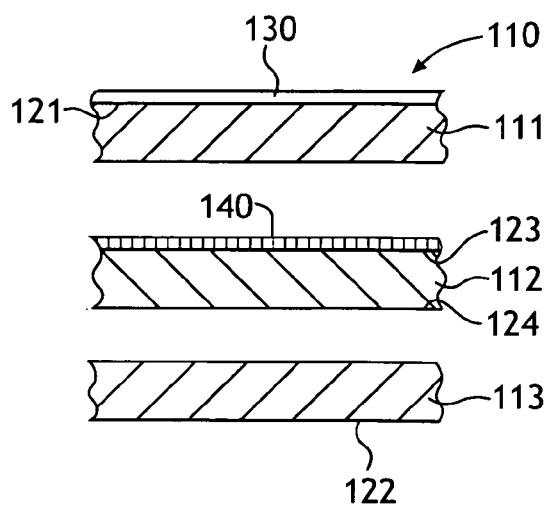

FIG. 2E shows a multi-ply tissue product 110 having a first outer ply 111, an inner ply 112, and a second outer ply 113. The inner surface 123 of the inner ply 112 is treated with an antimicrobial effective amount of an antimicrobial agent 140. The outer surface 121 of the first outer ply 111 is treated with an irritation-inhibiting composition 130. It is understood that the outer surface 122 of the second outer ply 113 may be treated with the irritation-inhibiting composition 130 in place of the treatment of the outer surface 121 of the first outer ply 111. It is also understood that the inner surface 124 of the inner ply 112 may be treated with an antimicrobial effective amount of an antimicrobial agent 140 in place of the treatment of the inner surface 123 of the inner ply 112.

FIG. 2F shows a multi-ply tissue product 110 having a first outer ply 111, an inner ply 112, and a second outer ply 113. The first outer ply 111 is treated with an antimicrobial effective amount of an antimicrobial agent 140. The outer surface 121 of the first outer ply 111 is treated with an irritation-inhibiting composition 130. It is understood that the outer surface 122 of the second outer ply 113 may be treated with the irritation-inhibiting composition 130 in place of the treatment of the outer surface 121 of the first outer ply 111. It is also understood that the second outer ply 113 may be treated with an antimicrobial effective amount of an antimicrobial agent 140 in place of the treatment of the first outer ply 111.

Figure 2G:
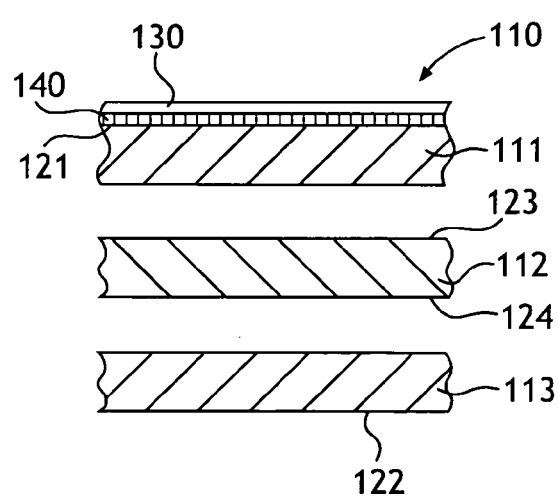

FIG. 2G shows a multi-ply tissue product 110 having a first outer ply 111, an inner ply 112, and a second outer ply 113. The outer surface 121 of the first outer ply 111 is treated with an antimicrobial effective amount of an antimicrobial agent 140. The outer surface 121 of the first outer ply 111 is then treated with an irritation-inhibiting composition 130 such that the irritation-inhibiting composition 130 is applied over the antimicrobial agent 140. It is understood that the outer surface 122 of the second outer ply 113 may be treated with an antimicrobial effective amount of an antimicrobial agent 140 in place of the treatment of the outer surface 121 of the first outer ply 111 and then the outer surface 122 of the second outer ply 113 may be treated with the irritation-inhibiting composition 130 in place of the treatment of the outer surface 121 of the first outer ply 111.

Figure 3:
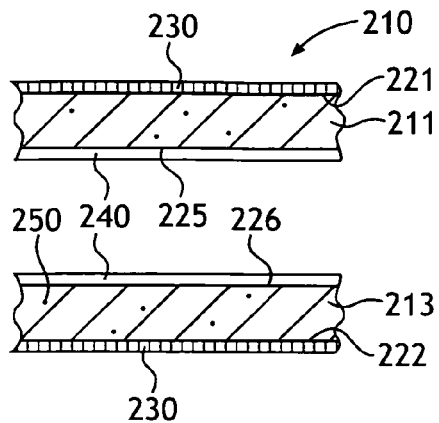
FIG. 3 is a diagram of a tissue product having two plies according to another embodiment of the present invention; and, FIGS. 3A-3I are diagrams showing different configurations of a tissue product having two plies according to another embodiment of the present invention.

FIG. 3 illustrates another embodiment of the present invention. The multi-ply tissue product 210 of this embodiment has two outer plies 211 and 213. At least one of the outer surfaces 221 and 222 of the outer plies 211 and 213, respectively, is treated with the irritation-inhibiting composition 230 comprising at least an irritation-inhibiting agent selected from an emollient, wax, solid fatty acid ester, fatty alcohol, hydrogenated animal or vegetable oil, lotion formulation, or mixture thereof. In this embodiment, there is no inner ply. The inner surfaces 225 and 226 of the outer plies 211 and 213, respectively, are defined by the inward facing surfaces of the outer plies 211 and 213, respectively. At least one of the inner surfaces 225 and 226 is treated with an antimicrobial agent 240. As in the second embodiment of the present invention, the contaminant 250 is readily absorbed onto at least one of the inner surfaces 225 and 226 wherein the contaminant 250 comes into contact with the antimicrobial agent 240, thus killing or otherwise inactivating the microorganisms within the contaminant 250 and preventing further exposure to the user.

Figure 3C:
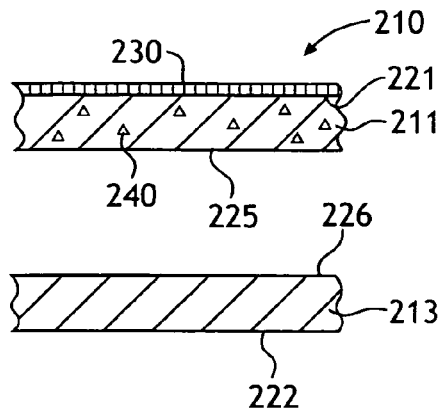
Figure 3A:
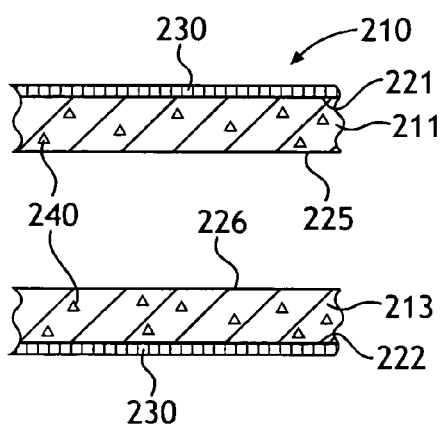

FIG. 3A shows a multi-ply tissue product 210 having two outer plies 211 and 213. The outer surfaces 221 and 222 of the outer plies 211 and 213, respectively, are treated with the irritation-inhibiting composition 230. The outer plies 211 and 213 are treated with an antimicrobial agent 240.

Figure 3D:
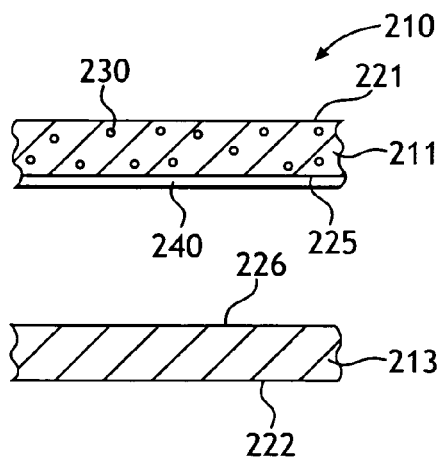
Figure 3B:
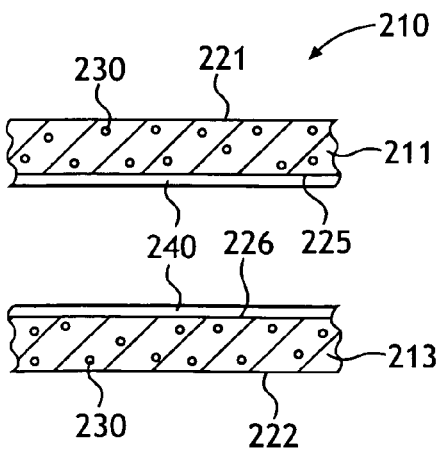

FIG. 3B shows a multi-ply tissue product 210 having two outer plies 211 and 213. The outer plies 211 and 213 are treated with the irritation-inhibiting composition 230. The inner surfaces 225 and 226 of the outer plies 211 and 213, respectively, are treated with an antimicrobial agent 240.

FIG. 3C shows a multi-ply tissue product 210 having two outer plies 211 and 213. The outer surface 221 of the outer ply 211 is treated with the irritation-inhibiting composition 230. The outer ply 211 is treated with an antimicrobial agent 240. It is understood that the outer surface 222 of the outer ply 213 may be treated with the irritation-inhibiting composition 230 in place of the treatment of the outer surface 121 of the outer ply 211. It is also understood that the outer ply 213 may be treated with the antimicrobial agent 240 in place of the treatment of the outer ply 211.

FIG. 3D shows a multi-ply tissue product 210 having two outer plies 211 and 213. The outer ply 211 is treated with the irritation-inhibiting composition 230. The inner surface 225 of the outer ply 211 is treated with an antimicrobial agent 240. It is understood that the inner surface 226 of the outer ply 213 may be treated with the antimicrobial agent 240 in place of the treatment of the inner surface 225 of the outer ply 211. It is also understood that the outer ply 213 may be treated with the irritation-inhibiting composition 230 in place of the treatment of the outer ply 211.

Figure 3E:
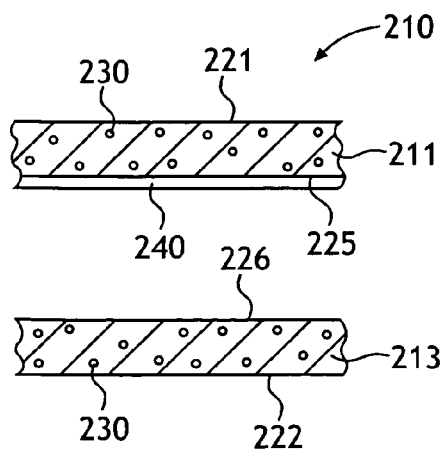

FIG. 3E shows a multi-ply tissue product 210 having two outer plies 211 and 213. The outer plies 211 and 213 are treated with the irritation-inhibiting composition 230. The inner surface 225 of the outer ply 211 is treated with an antimicrobial agent 240. It is understood that the inner surface 226 of the outer ply 213 may be treated with the antimicrobial agent 240 in place of the treatment of the inner surface 225 of the outer ply 211.

Figure 3F:
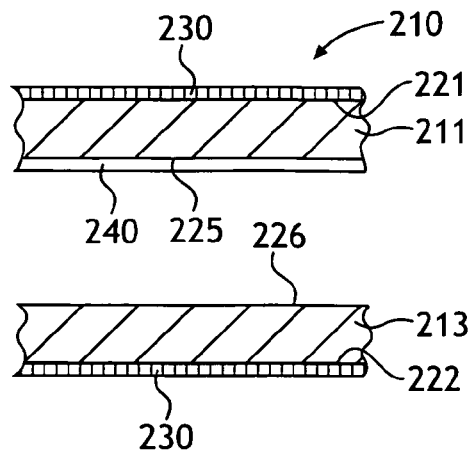

FIG. 3F shows a multi-ply tissue product 210 having two outer plies 211 and 213. The outer surfaces 221 and 222 of the outer plies 211 and 213, respectively, are treated with the irritation-inhibiting composition 230. The inner surface 225 of the outer ply 211 is treated with an antimicrobial agent 240. It is understood that the inner surface 226 of the outer ply 213 or both the inner surfaces 225 and 226 of the outer plies 211 and 213, respectively, may be treated with the antimicrobial agent 240 in place of the treatment of the inner surface 225 of the outer ply 213.

Figure 3H:
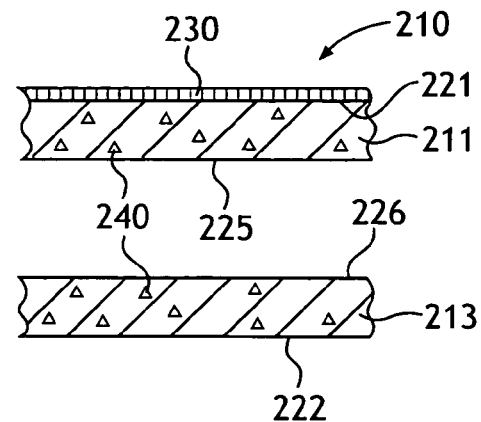
Figure 3G:
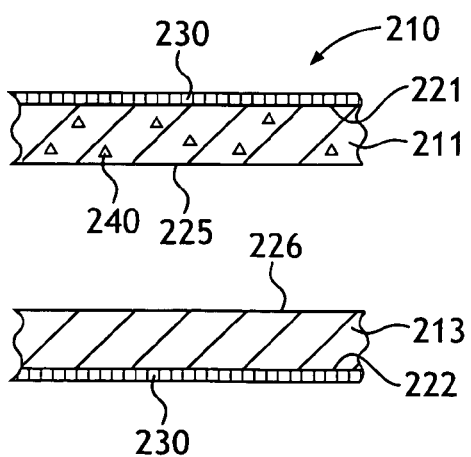

FIG. 3G shows a multi-ply tissue product 210 having two outer plies 211 and 213. The outer surfaces 221 and 222 of the outer plies 211 and 213, respectively, are treated with the irritation-inhibiting composition 230. The outer ply 211 is treated with an antimicrobial agent 240. It is understood that the outer ply 213 may be treated with the antimicrobial agent 240 in place of the treatment of the outer ply 211.

FIG. 3H shows a multi-ply tissue product 210 having two outer plies 211 and 213. The outer surface 221 of the outer ply 211 is treated with the irritation-inhibiting composition 230. The outer plies 211 and 213 are treated with an antimicrobial agent 240. It is understood that the outer surface 222 of the outer ply 213 may be treated with the irritation-inhibiting composition 230 in place of the treatment of the outer surface 221 of the outer ply 211.

Figure 3I:
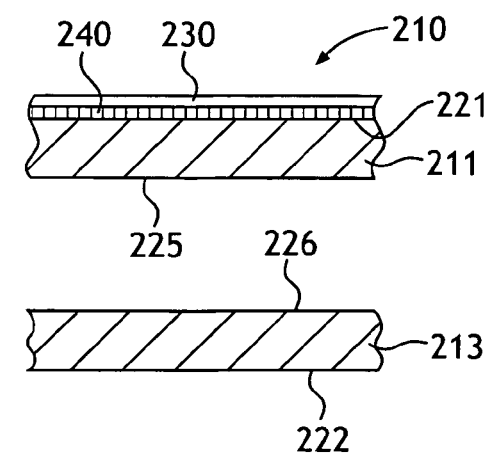

FIG. 3I shows a multi-ply tissue product 210 having two outer plies 211 and 213. The outer surface 221 of the outer ply 211 is treated with an antimicrobial agent 240. The outer surface 221 of the outer ply 211 is then treated with an irritation-inhibiting composition 230 such that the irritation-inhibiting composition 230 is applied over the antimicrobial agent 240. It is understood that the outer surface 222 of the outer ply 213 or both of the outer surfaces 221 and 222 of the outer plies 211 and 213, respectively, may be treated with the antimicrobial agent 240 in place of the treatment of the outer surface 221 of the outer ply 211 wherein the surfaces treated with the antimicrobial agent 240 are then treated with the irritation-inhibiting composition 230.

Antimicrobial Agent

The antimicrobial agent may comprise any of the virucides, bacteriocides, germicides, fungicides, and disinfectants known in the art. The selection of any particular antimicrobial agent will be dependent on its efficacy versus relevant microorganisms, human safety and toxicological profile, and environmental safety and toxicological profile. Of special interest as antimicrobial agents in the present invention are organic acids.

Suitable antimicrobial agents for the present invention include virucidal compositions. The virucidal compositions may include, without limitation, the carboxylic acid or the carboxylic acid/surfactant compositions disclosed in U.S. Pat. No. 4,975,217, issued to Brown-Skrobot et al.; U.S. Pat. No. 4,828,912, issued to Hossain et al.; U.S. Pat. No. 4,897,304, issued to Hossain et al.; U.S. Pat. No. 4,764,418, issued to Kuenn et al.; and, U.S. Pat. No. 4,738,847, issued to Rothe et al. The specification and claims of which are each hereby incorporated herein by reference in their entirety into this specification as if fully set forth herein.

As used herein, an antimicrobial carboxylic acid is a material that is capable of killing or otherwise inactivating such viruses as rhinovirus and influenza. Carboxylic acids that may be used as antimicrobials in the present invention include, without limitation, the compounds having the structure:

wherein R is a radical selected from the group consisting of $C_1$-$C_6$ alkyl, substituted $C_1$-$C_6$ alkyl, carboxy $C_1$-$C_6$ alkyl, carboxyhydroxy $C_1$-$C_6$ alkyl, carboxy halo $C_1$-$C_6$ alkyl, carboxy dihydroxy $C_1$-$C_6$ alkyl, dicarboxyhydroxy $C_1$-$C_6$ alkyl, $C_1$-$C_6$ alkenyl, carboxy $C_1$-$C_6$ alkenyl, dicarboxy $C_1$-$C_6$ alkenyl, phenyl, and substituted phenyl radicals. The hydrogen atoms of any of the above compounds may be substituted by one or more functional groups such as halogen atoms, hydroxyl groups, amino groups, thiol groups, nitro groups, and cyano groups, and the like.

The antimicrobial agent of the present invention may include, without limitation, the compounds having the structure:

R—COOR' wherein R is selected from the group consisting of: a radical selected from the group consisting of $C_1$-$C_6$ alkyl, substituted $C_1$-$C_6$ alkyl, carboxy $C_1$-$C_6$ alkyl, carboxyhydroxy $C_1$-$C_6$ alkyl, carboxy halo $C_1$-$C_6$ alkyl, carboxy dihydroxy $C_1$-$C_6$ alkyl, dicarboxyhydroxy $C_1$-$C_6$ alkyl, $C_1$-$C_6$ alkenyl, carboxy $C_1$-$C_6$ alkenyl, dicarboxy $C_1$-$C_6$ alkenyl, phenyl, and substituted phenyl radicals; and, R' is selected from the group consisting of: hydrogen atom; halogen atoms; hydroxyl groups; amino groups; thiol groups; nitro groups; and, cyano groups.

More specifically the organic acids that may be used as antimicrobial agents in the present invention include, but are not limited to: citric acid; malic acid; maleic acid; tartaric acid; salicylic acid; glycolic acid; adipic acid; glutaric acid; succinic acid; benzoic acid; lactic acid; and, mixtures thereof. Alphahydroxy and betahydroxy acids are also suitable for use as antimicrobial agents in the present invention.

The carboxylic acids may be present in the tissue product in any amount which is antimicrobially effective. The term "antimicrobially effective amount" means an amount sufficient to cause a 3 log drop in rhinovirus type 16 within 20 minutes in accordance with the Virucidal Assay Test described in the above-identified U.S. Pat. No. 4,897,304 and Canadian Patent No. 1,188,225, although those skilled in the art of virology will recognize other suitable test procedures for this purpose. The addition rate of the antimicrobial agent to the tissue surface may range from about 0.1 to about 10 mg/in$^2$. Alternatively, the addition rate of the antimicrobial agent to the tissue surface may range from about 0.3 to about 8.0 mg/in$^2$. In another alternative, the addition rate of the antimicrobial agent to the tissue surface may range from about 0.5 to about 5.0 mg/in$^2$.

The carboxylic acids may be combined with a surfactant. Carboxylic acid/surfactant antimicrobials are effective at add-on rates as low as 0.5 mg/in$^2$. The surfactant may be cationic, anionic, or nonionic. The nonionic surfactants may include, without limitation, the polyoxyethylenated alkylphenols such as TRITON X-100®, manufactured by Union Carbide of Danbury, Conn., and the polyoxyethylenated sorbitol esters such as TWEEN 40®, manufactured by Uniquema of Wilmington, Del. The cationic surfactants may include, without limitation, cetylpyridinium chloride ($C_5H_5N^+(CH_2)_{15}CH_3Cl^-$), dimethylbenzethonium quaternary ammonium chloride ($Me_3CCH_2C(Me)_2C_6H_3(Me)$-$OCH_2CH_2OCH_2CH_2{}^+N(Me)_2H_2C_6H_5Cl^-$). The anionic surfactants may be represented by the structures:

$(ROSO_3)_xM^+$ or $(RSO_3)_xM^+$ wherein, M$^+$ is a mono-, di- or tri-valent metal cation or an ammonium or substituted ammonium ion; x is an integer; and R is an alkyl group; or

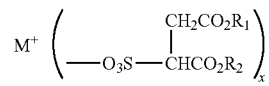

wherein, M$^+$ and x are defined as above and R$_1$ and R$_2$ may be the same or different and may be represented by straight or branched chain aliphatic groups.

More specifically, the anionic surfactants include secondary alkane sulfonates and sarcosinate surfactants. In some embodiments of the present invention, the anionic surfactants may include sodium dodecyl sulfate ($CH_3(CH_2)_{10}$—$CH_2OSO_3$—Na), and the 1,4-bis(2-ethylhexyl) ester, sodium salt of sulfosuccinic acid, as manufactured by Cytec Industries of West Paterson, N.J., under the tradename of AEROSOL OT. The above surfactants are presented in an illustrative rather than a limiting sense.

The antimicrobial agent may be any such material or compound which may be applied to the tissue product in a uniform manner, as by wet-end addition, embossing, spraying, coating, dipping, printing, or any other method known to those skilled in the art and which will not interfere with the irritation-inhibiting effectiveness of the tissue product to the extent that the tissue product is no longer pleasing during use to the consumer. The application of the antimicrobial agent may be uniform, in discreet modified zones, or other patterns such as stripes, dots, corrugated patterns, and the like.

In order to further optimize the antimicrobial effectiveness of the tissue product, blends of two or more of the antimicrobial agents may be applied to the surface of the tissue product. In one particular example, a blend of citric acid and malic acid may be used. The ratio of the citric acid to the malic acid may be from about 10 to about 1, more specifically from about 1 to about 1, or alternatively, from about 1 to about 10.

The add-on rate of the antimicrobial agent to the multi-layer tissue product is from about 0.5 percent to about 15 percent antimicrobial agent solids. More specifically, the add-on rate of the antimicrobial agent to the multi-layer tissue product is from about 3 percent to about 12 percent antimicrobial agent solids. Most specifically, the add-on rate of the antimicrobial agent to the multi-layer tissue product is from about 5 percent to about 10 percent antimicrobial agent solids.

The add-on rate of the antimicrobial agent to the multi-ply tissue product is from about 1 percent to about 15 percent antimicrobial agent solids. More specifically, the add-on rate of the antimicrobial agent to the multi-ply tissue product is about 3 percent to about 12 percent antimicrobial agent solids. Most specifically, the add-on rate of the antimicrobial agent to the multi-ply tissue product is from about 5 percent to about 10 percent antimicrobial agent solids.

Other additives may also be added to the antimicrobial agent. In some embodiments of the present invention, the antimicrobial agent includes humectants. For purposes herein, the term "humectant" means a hygroscopic compound or material which has an affinity for water and acts to stabilize the moisture content of the tissue product in the presence of fluctuating humidity. The presence of humectants can inhibit age-induced reduction in softness in the tissue products containing organic acids, particularly under conditions of low humidity (less than 35% relative humidity). Suitable humectants include, but are not limited to: aloe; polyethyleneglycols (as hereinafter defined); butylene glycol; propylene glycol and other glycols and their derivatives; sorbitol and its derivatives; dextrose and its derivatives; fructose and its derivatives; lactic acid and its salts; chitosan and its derivatives; glycerin and its derivatives; salts of carboxylic acid; ethoxylated dimethicone; and, hydrogenated starch hydrolysate.

Irritation-Inhibiting Agents

The irritation-inhibiting agent serves to mitigate the irritation or sting from the anitmicrobial agent in the multi-layer and multi-ply tissue product and may contribute to a soft, pleasing, smooth, soothing, non-irritating quality as well providing skin health benefits like moisturization, skin conditioning, protection, and the like. Suitable irritation-inhibiting agents include, but are not limited to: emollients; waxes; solid fatty acid esters; solid fatty alcohols; hydrogenated animal or vegetable oils and their derivatives; glycerin and its derivatives; glycols and their derivatives; liquid polyethylene glycols; ethoxylated polydimethylsiloxanes; quaternary ammonium compounds; botanical extracts with anti-irritant properties; lotion compositions; and, mixtures thereof. The irritation-inhibiting compositions containing the irritation-inhibiting agent(s) desirably will comprise high viscosity liquids or emulsions, gels, semi-solids, or solids at room temperatures and which are capable of being extruded, coated, or sprayed as a liquid and stay off the surface of the outer layer or outer ply of the tissue product.

The emollients that may be used as irritation-inhibiting agents of the present invention include, but are not limited to: petrolatum; mineral oil; non-hydrogenated vegetable or animal oils; liquid fatty alcohols; liquid fatty acids; polydimethylsiloxanes, organo-modified silicones; silicone gums; silicone resins; silicone elastomer; synthetic oils; triglycerides; triacetin; liquid fatty alcohols; branched fatty alcohols; branched esters; glyceryl esters and their derivatives; gurbet esters; lanolin and its derivatives; liquid fatty acid esters, such as isopropyl palmitate, octyl palmitate, isopropyl myristate, myristyl myristate, cetyl lactate, and the like; other emollient esters; and, mixtures thereof.

The waxes that may be used as irritation-inhibiting agents of the present invention include but are not limited to: bayberry wax; cerasin; ozokerite; fluorinated waxes; paraffin; polyethylene; $C_{28}$ or greater isoparaffins; ceresin; rice bran wax; microcrystalline wax; beeswax; japan wax; carnauba wax; montan acid wax; shellac wax; spent grain wax; ozokerite; synthetic waxes; ouricury wax; alkyl silicone waxes; lanolin wax; wax derivatives such as PEG beeswaxes, PEG carnauba waxes, and hydrogenated vegetable and animal oils; and, mixtures thereof.

The fatty alcohols that may be used as irritation-inhibiting agents of the present invention include, but are not limited to: cetearyl alcohol; cetyl alcohol; stearyl alcohol; arachidyl alcohol; behenyl alcohol; myristyl alcohol; lanolin alcohols; $C_{20}$ to $C_{40}$ alcohols; and, mixtures thereof.

The solid fatty acid esters that may be used as irritation-inhibiting agents of the present invention include, but are not limited to: cetyl esters; behenyl benzoate; stearyl benzoate; behenyl behenate; arachidyl behenate; $C_{20}$ to $C_{40}$ alkyl behenate; $C_{20}$ to $C_{40}$ alkyl benzoate; stearyl behenate; cetyl lactate; myristyl myristate; $C_{12}$ to $C_{15}$ alkyl lactate; $C_{20}$ to $C_{40}$ alkyl stearate; stearyl stearate; and, mixtures thereof.

The hydrogenated animal or vegetable oils and their derivatives that may be used as irritation-inhibiting agents of the present invention include, but are not limited to: hydrogenated palm triglycerides; hydrogenated castor oil; hydrogenated palm oil; hydrogenated cottonseed oil; hydrogenated jojoba oil; hydrogenated mink oil; hydrogenated rice bran wax; hydrogenated vegetable oil; hydrogenated castor oil laurate; hydrogenated castor oil, triiostearin esters; hydrogenated avocado oil; hydrogenated rapeseed oil; hydrogenated soybean oil; and, mixtures thereof.

The botanical extracts and other anti-irritant compounds that may be used as irritation-inhibiting agents of the present invention include, but are not limited to: cucumber extract; quercetin; sage extract; ubiquinone; green tea; Grapeseed extract; Canadian willow herb extract; polyphenols; rutin; silymarin; azulene; and, mixtures thereof.

Many of the irritation-inhibiting agents may be applied to the outer layer or ply of the tissue product alone or in combination with other components. However, in order to prevent migration of the irritation-inhibiting agent(s) into the inner portion of the layer or ply of the tissue product, the irritation-inhibiting agent(s) may be necessary to formulate the irritation-inhibiting agent(s) into a composition that contains a structuring or solidifying agent. Additionally, these compositions may contain solvents, surfactants, stabilizers, viscosity/rheology modifiers, melting point modifiers, suspending agents, anti-oxidants, colorants, preservatives and fragrances, skin protectants, and/or other agents to achieve the desired physical properties and provide other skin health benefits. In this regard, the irritation-inhibiting compositions should have a melting point of at least about 25° C. and specifically has a melting point between about 30° C. and about 100° C., and still more specifically, between about 55° C. and about 70° C. thereby providing improved stability of the composition and transfer of the composition to the skin of the user. Irritation-inhibiting compositions having lower melting points may exhibit migration of the composition at elevated storage temperatures that may undesirably result in reduced transfer to the user's skin.

However, in some embodiments of the present invention, the compositions containing the irritation-inhibiting agent(s) may transfer to the user's skin during use of the tissue product. The compositions containing irritation-inhibiting agent(s) should not be so solid nor adhere so strongly to the layer or ply of the tissue product that the composition is prevented from being transferred from the surface to the user's skin during use. In this regard, the penetration hardness of the irritation-inhibiting agent ranges between about 5 and about 350 millimeters, more specifically between about 40 and about 150 millimeters.

In one embodiment of the present invention, the multi-ply or multi-layer tissue product may be treated with a hydrophilic irritation-inhibiting composition on the outer surface of an outer ply or layer wherein the hydrophilic irritation-inhibiting composition comprises from about 10 to about 100 weight percent of an irritation-inhibiting agent(s), from about 10 to about 90 weight percent of a hydrophilic solvent, from about 5 to about 90 weight percent of a solidifying agent being a polyethylene glycol or a derivative thereof which is a solid at 20° C. (primary function to solidify the irritation-inhibiting composition so that the irritation-inhibiting composition is a solid at room temperature) and has a molecular weight of at least about 720 and optionally, a fatty alcohol or fatty acid having a chain length of from about $C_{14}$ to $C_{30}$. The hydrophilic solvent may comprise, but is not limited to: propylene glycol; butylene glycol; triethylene glycol; diethylene glycol; hexylene glycol; propane diol; low molecular weight (less than 720) polyethylene glycols; glycerin; hydrogenated starch hydrolysate; and, mixtures thereof. The fatty alcohol typically comprises an alcohol having a carbon chain length of from about $C_{14}$ to $C_{30}$, including, but not limited to: cetyl alcohol; stearyl alcohol; arachidyl alcohol; benhenyl alcohol; lanolin alcohol; and, mixtures thereof. The fatty acid typically comprises an acid having a carbon chain length of from about $C_{14}$ to $C_{30}$, including, but not limited to: palmitic acid; stearic acid; benhenic alcohol; lanolin acid; and, mixtures thereof. In some embodiments, it may be necessary to use a low HLB surfactant to emulsify small amounts lipophilic materials into a hydrophilic irritation-inhibiting composition.

In other embodiments of the present invention, the addition of a viscosity/rheology modifier may be desired to prevent the migration of the hydrophilic irritation-inhibiting composition into the layer or ply of the tissue product at elevated temperatures like the temperatures encountered during transportation and storage. Suitable viscosity/rheology modifiers include, but are not limited to: talc; clays; organically modified clays; magnesium aluminum silicate; metal soaps; carrageenan gums, such as xantham gum; cellulose thickeners; allyl ethers of pentaerythritol; an ally ether of sucrose or an allyl ether of propylene thickener; and, mixtures thereof.

Hydrophilic irritation-inhibiting compositions of this type are described in more detail in the U.S. Pat. No. 5,869,075 issued to Krzysik on Feb. 9, 1999. The specification and claims of which is hereby incorporated herein by reference in their entirety into this specification as if fully set forth herein.

According to another embodiment of the present invention, the multi-ply or multi-layer tissue product may be treated with a hydrophobic irritation-inhibiting composition on 95 percent or less of the outer surface of an outer ply or layer wherein the hydrophobic irritation-inhibiting composition surface of an outer ply or layer wherein the hydrophobic irritation-inhibiting composition comprises from about 10 to about 90 weight percent of an irritation-inhibiting agent(s), from about 10 to about 90 weight percent of an emollient, from about 5 to about 85 weight percent of a solidifying agent and optionally, a fatty alcohol having a chain length of from about $C_{14}$ to $C_{30}$. Suitable emollients include, but are not limited to: petrolatum based oils; vegetable based oils; animal based oils; mineral oils; silicones; synthetic oils; lanolin and its derivatives; esters; branched esters; gurbet esters; fatty acids; fatty acid esters; triglycerides; alkyl hydroxystearates; and, mixtures thereof. Suitable solidifying agents whose primary function is to solidify the hydrophobic irritation-inhibiting composition so that the hydrophobic irritation-inhibiting composition is a solid at room temperatures, include, but are not limited to: about $C_{16}$ or greater alkyl silicones; fatty acid esters with a melting point of at least about 35° C.; about $C_{16}$ or greater alkyl hydroxystearates; alkoxylated alcohols; alkoxylated carboxylic alcohols; hydrogenated animal or vegetable oils; waxes and modified waxes such as bayberry wax, beeswax, carnauba wax, ceresin, lanolin wax, paraffin, rice bran wax, synthetic spermaceti wax, cerasin, ozokerite, polyethylene, $C_{28}$ and greater isoparaffins, microcrystalline wax, shellac wax, montan acid wax, fluoranated waxes; and, mixtures thereof. Such hydrophobic irritation-inhibiting compositions are described more detail in the U.S. Pat. No. 5,665,426 issued to Krzysik et al.; U.S. Pat. No. 5,650,218 issued to Krzysik et al; and, U.S. patent application Ser. No. 10/659,968 filed on Sep. 11, 2003 to Krzysik et al. The specification and claims of which are each hereby incorporated herein by reference in their entirety into this specification as if fully set forth herein.

In some embodiments of the present invention, the addition of a viscosity/rheology modifier may be desired to prevent the migration of the hydrophobic irritation-inhibiting composition into the layer or ply of the tissue product at elevated temperatures such as the temperatures encountered during transportation and storage. Suitable viscosity/rheology modifiers include, but are not limited to: polyolefin resins and polymers; polyethylene; polystyrene; ethylene/vinyl acetate copolymers; ethylene/propylene styrene copolymers; butylene/ethylene styrene copolymers; silica; treated silica; talc; organically modified clays; colloidal silicon dioxide; and, mixtures thereof.

In some embodiments of the present invention, it may be necessary to use a medium HLB surfactant to emulsify small amounts of hydrophilic materials into a hydrophilic irritation-inhibiting composition. The hydrophilic irritation-inhibiting composition comprises from about 10 to about 100 weight percent of an hydrophobic irritation-inhibiting agent(s); from about 10 to about 90 weight percent of a hydrophobic emollient; from about 5 to about 90 weight percent of a structurant or solidifying agent having a melting point of about 35° C. to about 75° C. selected from the group of waxes, modified waxes, synthetic waxes, polymer waxes, vegetable waxes, fatty alcohols, fatty acids and fatty acid esters, and mixtures thereof; and, a rheology modifier selected from the group of silica, polyethylene, ethylene vinyl acetate copolymers, polyethylene, alpha-olefin modified polyethylene, organo-clays, and mixtures thereof. Hydrophilic irritation-inhibiting compositions of this type are described in more detail in the U.S. Pat. No. 5,869,075 issued to Krzysik on Feb. 9, 1999. The specification and claims of which is hereby incorporated herein by reference in their entirety into this specification as if fully set forth herein.

Absorption Enhancing Agent

The absorption enhancing agent enables or facilitates the absorption of the contaminant into the multi-layer and multi-ply tissue product such that the contaminant contacts the antimicrobial agent wherein the contaminant is killed or otherwise inactivated.

The absorption enhancing agents that may be used in the present invention may include, without limitation: alkyl sulfates; primary and secondary alkane sulfonates; alkyl diphenyl oxide disulfonates; alkyl benzene sulfonates; alkylsulfonates; isothionates; alkylethersulfates; α-olefin sulfonates; alkyl taurates; alkyl sarcosinates; Isolaureth-6; polyalkyleneoxide modified polydimethylsiloxane; alkylpolyethyleneoxide ethanol; 1-alkyl-2-pyrrolidone, alkylamidoalkylenedialkylamine oxide; trialkylamine oxide; alkylamidoalkyldialalkylbetaines; and, the like as well as mixtures thereof. The multi-layer or multi-ply tissue product treated with the absorption enhancing agents of the present invention provide an antimicrobially effective tissue product.

The addition rate of the absorption enhancing agents of the present invention to the tissue surface may range from about 0.1 to about 10 mg/in$^2$, from about 0.3 to about 8.0 mg/in$^2$, from about 0.5 to about 5.0 mg/in$^2$ and from about 0.5 to about 10.0 mg/in$^2$.

The add-on rate of the absorption enhancing agents of the present invention to the multi-layer tissue product is from about 0.5 percent to about 15 percent absorption enhancing agent solids. More specifically, the add-on rate of the absorption enhancing agent to the multi-layer tissue product is from about 3 percent to about 12 percent absorption enhancing agent solids. Most specifically, the add-on rate of the absorption enhancing agent to the multi-layer tissue product is from about 5 percent to about 10 percent absorption enhancing agent solids.

The absorption time of 0.1 gram of water into a multi-layer or multi-ply tissue product treated with the absorption enhancing agent is about 6 minutes or less, about 5 minutes or less, about 3 minutes or less, about 1 minute or less, about 30 seconds or less, about 10 seconds or less, about 5 seconds or less, about 3 seconds or less, about 1 second or less, about 0.8 second or less, about 0.5 or less, about 0.1 second or less. The absorption time may range from about 6 minutes to about 0.01 second, more specifically from about 5 minutes to about 0.1 second, more specifically from about 3 minutes to about 0.5 second, and most specifically from about 1 minute to about 0.8 second.

Additional Agents

The irritation-inhibiting agent or composition may be any such material or compound which can be applied to the tissue product in a uniform manner, as by wet-end addition, embossing, spraying, coating, dipping, printing, slot coating, or any other method known to those skilled in the art and which will not interfere with the antimicrobial effectiveness of the tissue product to the extent that the tissue product is no longer antimicrobial effective. The application of the irritation-inhibiting agent may be uniform, in discreet modified zones, or other patterns such as stripes, dots, corrugated patterns, and the like.

The low sheer viscosity range at process temperatures of the irritation-inhibiting agent or composition may be from about 100 centipoise to about 1,000,000 centipoise or higher, more specifically from about 1,000 to about 500,000 centipoise. The low shear viscosity range at room temperature of the irritation-inhibiting agent or composition may be from about 5,000 centipoise to about 2,000,000 or greater or is a solid, more specifically from about 50,000 centipoise to about 2,000,000 or is a solid.

In order to further optimize and balance the softness, sting mitigation, and skin benefits of the irritation-inhibiting agent, blends of two or more of the irritation-inhibiting agents may be applied to the surface of the multi-layer or multi-ply tissue product. In one particular example, a blend of petrolatum and stearyl alcohol may be used. The ratio of petrolatum to stearyl alcohol may be from about 4 to about 1, more specifically from about 7 to about 3, and most specifically from about 3 to about 2.

The add-on rate of the irritation-inhibiting agent or composition to the multi-layer or multi-ply tissue product is from about 1 percent to about 30 percent based on the weight of the tissue product. More specifically, the add-on rate of the irritation-inhibiting agent or composition to the multi-layer or multi-ply tissue product is about 3 percent to about 20 percent based on the weight of the tissue product. Most specifically, the add-on rate of the irritation-inhibiting agent to the multi-layer or multi-ply tissue product is about 5 percent to about 15 percent based on the weight of the tissue product.

The weight percentage amount of the irritation-inhibiting agent or composition can vary greatly, depending upon the desired tactile properties, the amount of the antimicrobial agent present that needs to be counteracted, the properties of the irritation-inhibiting agent or composition itself, and the like.

The tissue products of the present invention may be made by any method known by those skilled in the art. Various tissue products and methods of manufacturing tissue products are disclosed in the following U.S. Pat. Nos. 6,083,346 issued to Hermans et al.; 6,096,169 issued to Hermans et al.; 6,080,279 issued to Hada et al.; 3,953,638 issued to Kemp; 5,324,575 issued to Sultze; 5,656,134 issued to Marinack et al.; 5,685,954 issued to Marinack et al.; 5,690,788 issued to Marinack et al.; 5,336,373 to Scattolino et al.; 5,556,509 issued to Trokhan et al.; 5,709,775 issued to Trokhan et al.; 5,776,312 issued to Trokhan et al.; 5,837,103 issued to Trokhan et al.; 5,871,887 issued to Trokhan et al.; 4,637,859 issued to Trokhan et al.; 5,814,190 issued to Van Phan; 5,846,379 issued to Ampulski et al.; 5,885,415 issued to Marinack et al.; 5,885,417 issued to Marinack et al.; 5,779,860 issued to Hollenberg et al.; 5,048,589 issued to Cook et al.; 4,100,324 issued to Anderson et al.; and, 4,426,417 issued to Meitner et al. as well as the European Patents and Patent Applications: EP 0 677 612 A2 in the name of Wendt et al. and EP 0 631 014 B1 issued to Farrington, Jr. et al. and the U.S. patent application Ser. Nos. 09/751,329 filed on Dec. 29, 2000 entitled Composite Material with Cloth-like Feel; 09/564,449 filed on May 4, 2000 entitled Ion-Sensitive, Water Dispersible Polymers, A Method of Making Same and Items Using Same; and, 09/565,623 filed on May 4, 2000 entitled Ion-Sensitive Hard Water Dispersible Polymers and Applications Therefor. The specification and claims of which are each hereby incorporated by reference in their entirety into this specification as if fully set forth herein.

The present invention will be further illustrated with reference to the following specific example. It is understood that the example is given by way of illustration and is not meant to limit the disclosure or the claims that follow.

EXAMPLES

The hydrophilic irritation inhibiting compositions may include, without limitation:

|  | Example 1 Wt % | Example 2 Wt % | Example 3 Wt % |
| --- | --- | --- | --- |
| Propylene glycol | 60 | 40 | — |
| Polyethylene Glycol 400 | — | 10 | 50 |
| Polyethylene Glycol 8000 | 20 | 30 | 20 |
| Polyethylene Glycol 1000 | — | — | 30 |
| Stearyl Alcohol | 20 | — | — |
| Behenyl Alcohol | — | 20 | — |

|  | Example 4 Wt % | Example 5 Wt % | Example 6 Wt % |
| --- | --- | --- | --- |
| Propylene glycol | 60 | 40 | — |
| Silica | 2 | — | — |
| Laponite (synthetic Bentonite) | — | 5 | 2 |
| Glycerin | — | — | 5 |
| Polyethylene Glycol 400 | — | 10 | 50 |
| Polyethylene Glycol 6000 | 30 | 30 | 20 |
| Polyethylene Glycol 1000 | — | — | 23 |
| Stearyl Alcohol | — | — | — |
| Behenyl Alcohol | 10 | 15 | — |

The hydrophobic irritation inhibiting compositions may include, without limitation:

|  | Example 7 Wt % | Example 8 Wt % | Example 9 Wt % |
| --- | --- | --- | --- |
| Mineral Oil | 60 | — | — |
| Petrolatum | — | 60 | 40 |
| Octododecanol | — | — | 20 |
| Behenyl Alcohol | 20 | 40 | — |
| Cerasin | 20 | — | 20 |
| Cetyl Palmitate | — | — | 20 |

|  | Example 10 Wt % | Example 11 Wt % | Example 12 Wt % |
| --- | --- | --- | --- |
| Sunflower Oil | — | 20 | — |
| Petrolatum | 60 | 40 | 40 |
| Isopropyl palmitate | 5 | — | — |
| Ethylene Vinyl Acetate Copolymer | 5 | — | — |

-continued

| | | | |
|---|---|---|---|
| Silica | | 2 | 3 |
| Bentonite | — | — | 2 |
| Behenyl Behenate | — | — | 20 |
| Microcrystalline wax | 30 | 38 | 25 |
| Polyethylene | | | 10 |

We claim:

1. A non-irritating, antimicrobial, multi-ply tissue product comprising a first outer ply having an outer surface, a second outer ply having an outer surface, and one or more inner plies, wherein said first and second outer plies contain an amount of an irritation-inhibiting agent and sodium lauryl sulfate applied to the outer surfaces, wherein said one or more inner plies contain an antimicrobially effective amount of at least one antimicrobial agent; and wherein the at least one antimicrobial agent is confined to the one or more inner plies.

2. The facial tissue product of claim 1 having an absorption time is from about 6 minutes to about 0.1 second.

3. The facial tissue product of claim 1 having an absorption time is from about 5 minutes to about 0.1 second.

4. The facial tissue product of claim 1 having an absorption time is from about 3 minutes to about 0.5 second.

5. The facial tissue product of claim 1 having an absorption time is from about 1 minute to about 0.8 second.

6. The facial tissue of claim 1 wherein the antimicrobial agent has the structure:

R—COOR' wherein R is selected from the group consisting of: a radical selected from the group consisting of $C_1$-$C_6$ alkyl, substituted $C_1$-$C_6$ alkyl, carboxy $C_1$-$C_6$ alkyl, carboxyhydroxy $C_1$-$C_6$ alkyl, carboxy halo $C_1$-$C_6$ alkyl, carboxy dihydroxy $C_1$-$C_6$ alkyl, dicarboxyhydroxy $C_1$-$C_6$ alkyl, $C_1$-$C_6$ alkenyl, carboxy $C_1$-$C_6$ alkenyl, dicarboxy $C_1$-$C_6$ alkenyl, phenyl, and substituted phenyl radicals; and, R' is selected from the group consisting of: hydrogen atom; halogen atoms; hydroxyl groups; amino groups; thiol groups; nitro groups; and, cyano groups.

7. The facial tissue of claim 1 wherein the antimicrobial agent comprises an organic acid.

8. The facial tissue of claim 1 wherein the irritation-inhibiting agent is selected from the group consisting of: emollients; glycerin; glycols; liquid polyethylene glycols; ethoxylated polydimethylsiloxanes; quaternary ammonium compounds; botanical extracts; solid fatty acid esters; hydrogenated animal or vegetable oils; lotion compositions; waxes; solid fatty alcohols; and mixtures thereof.

9. The facial tissue of claim 8 wherein the antimicrobial agent comprises citric acid.

* * * * *